(12) United States Patent
Swartz et al.

(10) Patent No.: US 6,605,087 B2
(45) Date of Patent: Aug. 12, 2003

(54) ABLATION CATHETER

(75) Inventors: John F. Swartz, Afton, OK (US); Michael C. Bednarek, Buffalo, MN (US); Richard E. Stehr, Stillwater, MN (US)

(73) Assignee: St. Jude Medical, Daig Division, Minnetonka, MN (US)

( * ) Notice: Subject to any disclaimer, the term of this patent is extended or adjusted under 35 U.S.C. 154(b) by 0 days.

(21) Appl. No.: 09/906,861

(22) Filed: Jul. 17, 2001

(65) Prior Publication Data

US 2002/0016589 A1 Feb. 7, 2002

Related U.S. Application Data

(62) Division of application No. 09/361,811, filed on Jul. 27, 1999, now Pat. No. 6,264,654, which is a division of application No. 08/897,300, filed on Jul. 21, 1997, now Pat. No. 6,080,151.

(51) Int. Cl.⁷ ............................................... A61B 18/18
(52) U.S. Cl. .......................... 606/41; 607/101; 607/105
(58) Field of Search ............................... 606/41, 45, 49, 606/27, 28; 607/99, 105, 113, 122

(56) References Cited

U.S. PATENT DOCUMENTS

| | | |
|---|---|---|
| 4,161,952 A | 7/1979 | Kinney et al. |
| 4,641,649 A | 2/1987 | Walinsky et al. |

(List continued on next page.)

FOREIGN PATENT DOCUMENTS

| WO | WO 95/10319 | 4/1995 |
|---|---|---|

OTHER PUBLICATIONS

Singer, I., et al., "Catheter Ablation for Arrhythmias" *Clinical Manual of Electrophysiology* pp. 421–431 (1993).
Saul, J.P., et al., "Catheter Ablation of Accessory Atrioventricular Pathways in Young Patients: Use of Long Vascular Sheaths, the Transseptal Approach and a Retrograde Left Posterior Parallel Approach" *Journal of the American College of Cardiology*, vol. 21, No. 3, pp. 571–583 (Mar. 1, 1993).
Swartz, J.F., "Radiofrequency Endocardial Catheter Ablation of Accessory Atrioventricular Pathway Atrial Insertion Sites" *Circulation*, vol. 87, No. 2, pp. 487–499 (Feb., 1993).
Tracey, C.N. "Radio Frequency Catheter Ablation of Ectopic Atrial Tachycardia Using Paced Activation Sequence Mapping" *J. Am. Coll. Cardiol.* vol. 21, pp. 910–917 (1993).

*Primary Examiner*—Roy D. Gibson
(74) *Attorney, Agent, or Firm*—Scott R. Cox

(57) ABSTRACT

An ablation catheter is disclosed having proximal and distal ends and an external surface, a lumen contained within the catheter body, a plurality of openings in the surface of the catheter, wherein the openings are in communication with the lumen, one or more electrodes secured within the catheter within the lumen and a source for conductive media to be introduced into the lumen to contact the electrode. The ablation catheter also may contain a conductive media flow control system which controls the flow of the conductive media through the openings in the surface of the catheter. Also disclosed is a process for ablation of human tissue which includes introducing an ablation catheter into the human body to a location to be ablated, passing a conductive media through a lumen of the catheter to contact one or more electrodes, passing the conductive media through the openings in the catheter body to contact the tissue to be ablated, and conducting energy from the electrode through the conductive media to the tissue for a sufficient period of time to ablate the tissue.

20 Claims, 6 Drawing Sheets

U.S. PATENT DOCUMENTS

| | | |
|---|---|---|
| 4,776,334 A | 10/1988 | Prionas |
| 4,860,769 A | 8/1989 | Fogarty et al. |
| 4,892,102 A | 1/1990 | Astrinsky |
| 4,934,049 A | 6/1990 | Kiekhafer et al. |
| 4,945,912 A | 8/1990 | Langberg |
| 5,025,786 A | 6/1991 | Siegel |
| 5,047,026 A | 9/1991 | Rydell |
| 5,209,229 A | 5/1993 | Gilli |
| 5,228,442 A | 7/1993 | Imran |
| 5,231,995 A | 8/1993 | Desai |
| 5,242,441 A | 9/1993 | Avitall |
| 5,246,438 A | 9/1993 | Langberg |
| 5,263,493 A | 11/1993 | Avitall |
| 5,281,213 A | 1/1994 | Milder et al. |
| 5,281,217 A | 1/1994 | Edwards et al. |
| 5,281,218 A | 1/1994 | Imran |
| 5,293,868 A | 3/1994 | Nardella |
| 5,327,905 A | 7/1994 | Avitall |
| 5,334,193 A | 8/1994 | Nardella |
| 5,354,297 A | 10/1994 | Avitall |
| 5,380,319 A | 1/1995 | Saito et al. |
| 5,397,304 A | 3/1995 | Truckai |
| 5,433,708 A | 7/1995 | Nichols et al. |
| 5,460,628 A | 10/1995 | Neuwirth et al. |
| 5,487,385 A | 1/1996 | Avitall |
| 5,497,774 A | 3/1996 | Swartz et al. |
| 5,505,730 A | 4/1996 | Edwards |
| 5,507,725 A | 4/1996 | Savage et al. |
| 5,542,928 A | 8/1996 | Evans et al. |
| 5,545,193 A | 8/1996 | Fleischman et al. |
| 5,564,440 A | 10/1996 | Swartz et al. |
| 5,575,166 A | 11/1996 | Michalewski et al. |
| 5,575,766 A | 11/1996 | Swartz et al. |
| 5,628,316 A | 5/1997 | Swartz et al. |
| 5,640,955 A | 6/1997 | Ockuly et al. |
| 5,653,692 A | 8/1997 | Masterson et al. |
| 5,676,662 A | 10/1997 | Fleischhacker et al. |
| 5,676,693 A | 10/1997 | LaFontaine |
| 5,785,706 A | 7/1998 | Bednarek |
| 5,919,188 A | 7/1999 | Shearon et al. |
| 6,015,407 A | 1/2000 | Rieb et al. |
| 6,068,653 A | 5/2000 | LaFontaine |
| 6,080,151 A | 6/2000 | Swartz et al. |
| 6,106,522 A | 8/2000 | Fleischman et al. |
| 6,264,654 B1 | 7/2001 | Swartz et al. |

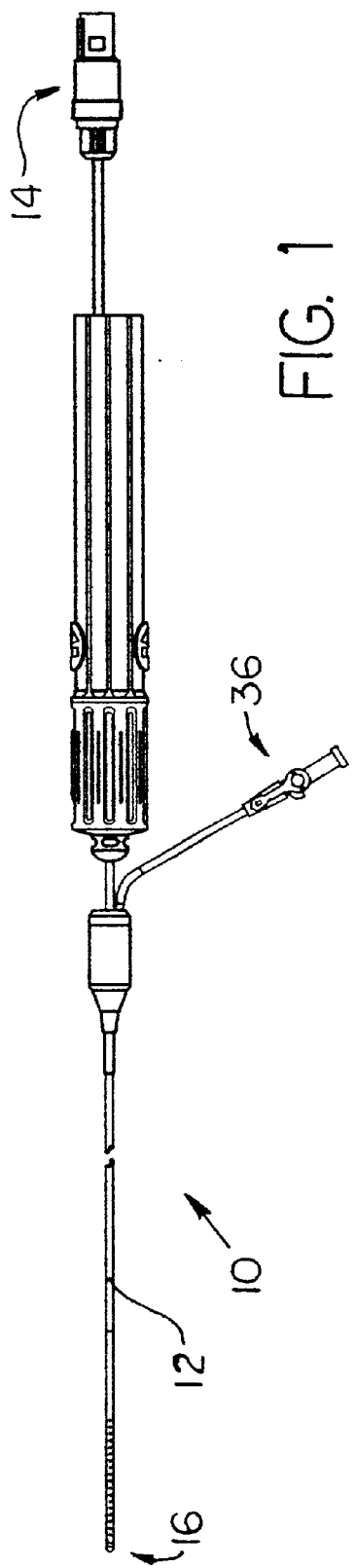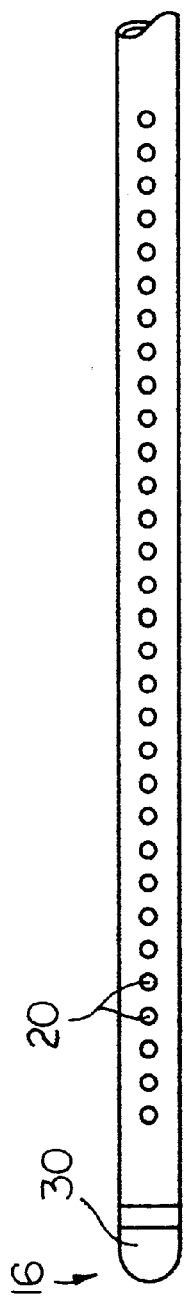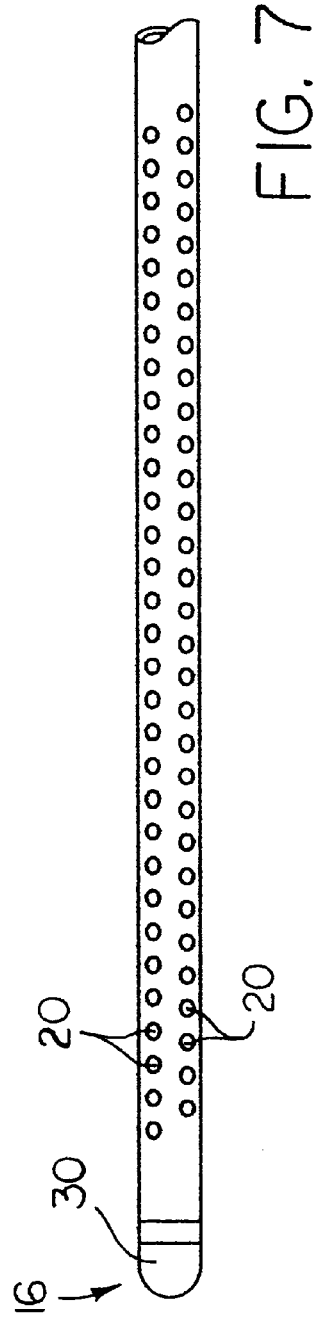

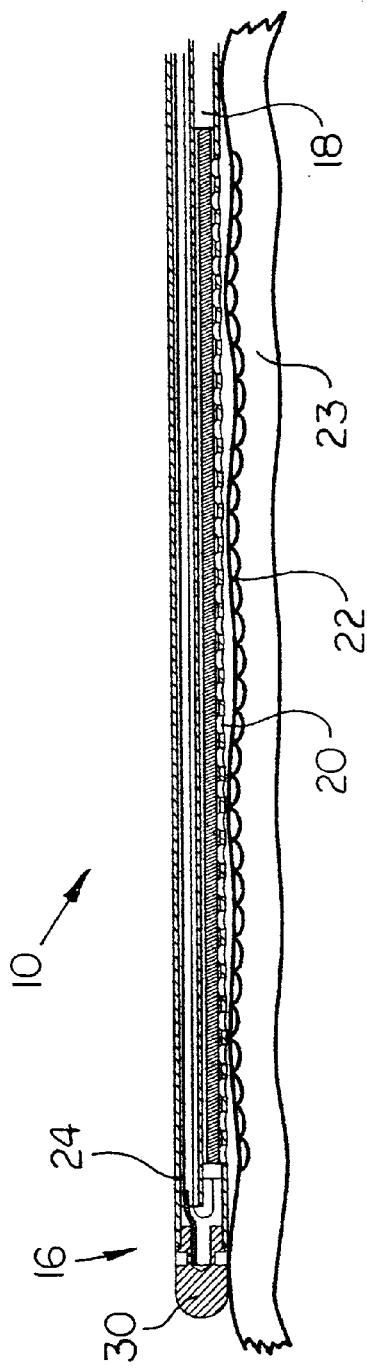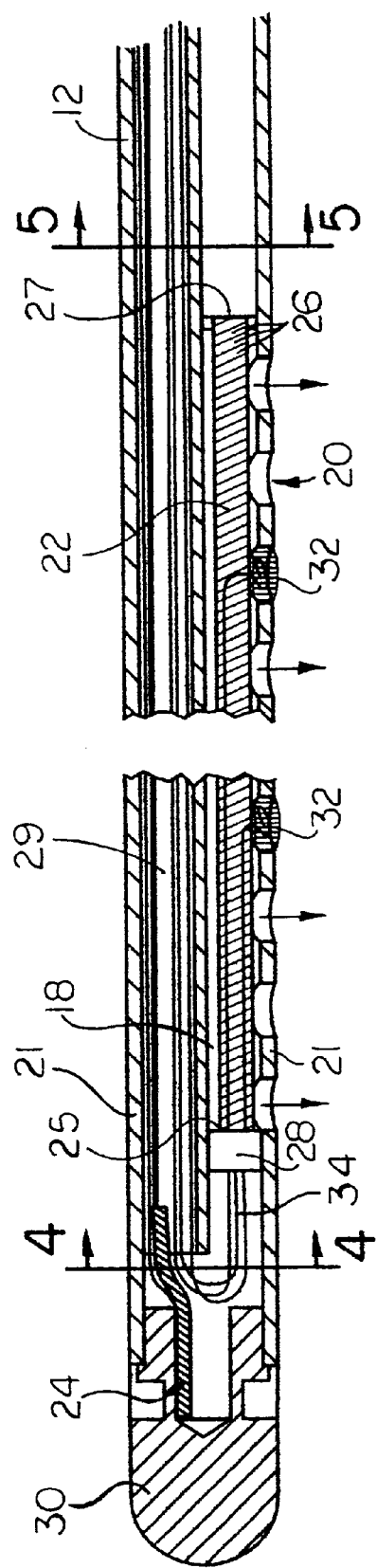

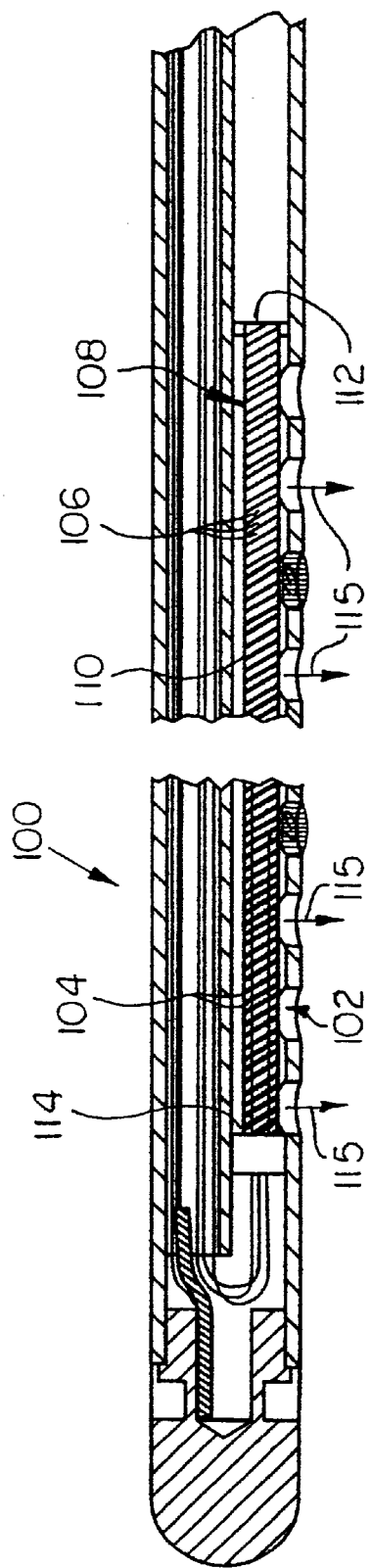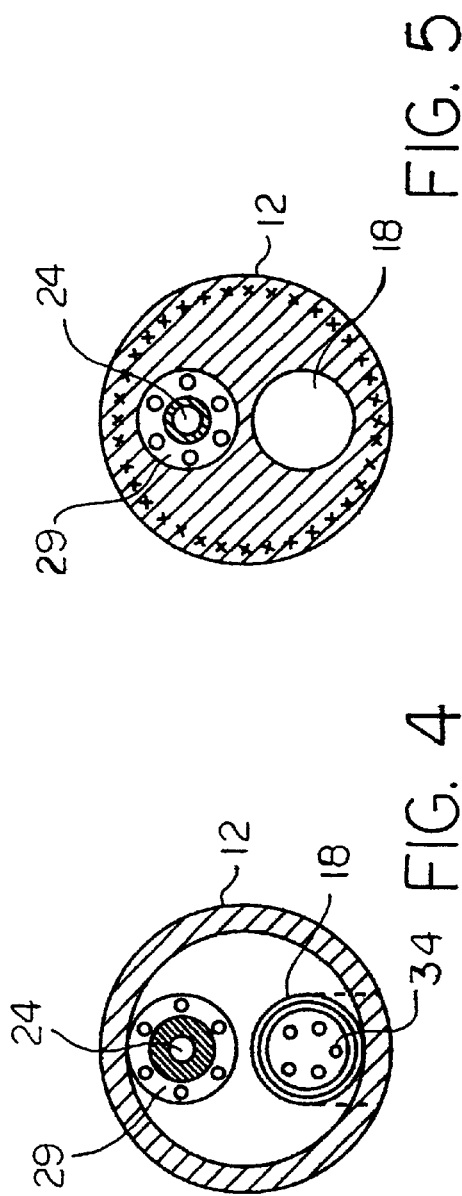

ABLATION CATHETER

This application is a divisional application Ser. No. 09/361,811 filed on Jul. 27, 1999, now U.S. Pat. No. 6,264,654, which is a divisional of application Ser. No. 08/897,300 filed Jul. 21, 1997 now U.S. Pat. No. 6,080,151

FIELD OF INVENTION

This invention relates to catheters for the mapping and ablation of human tissue, particularly cardiac tissue. In particular, the invention relates to an ablation catheter to ablate human tissue utilizing conductive media contacted by an electrode, which electrode is contained within the catheter.

BACKGROUND

Catheters have been in use for medical procedures for many years. Catheters can be used for medical procedures to examine, diagnose and treat while positioned at a specific location within the body which is otherwise inaccessible without more invasive procedures. During these procedures a catheter is inserted into a vessel near the surface of the body and is guided to a specific location within the body for examination, diagnosis and treatment. For example, one procedure utilizes a catheter to convey an electrical stimulus to a selected location within the human body. Another procedure utilizes a catheter with sensing electrodes to monitor various forms of electrical activity in the human body.

Catheters are also used increasingly for medical procedures involving the human heart. Typically, the catheter is inserted in an artery or vein in the leg, neck or arm of the patient and threaded, sometimes with the aid of a guidewire or introducer, through the vessels until a distal tip of the catheter reaches the desired location for the medical procedure in the heart.

A typical human heart includes a right ventricle, a right atrium, a left ventricle and a left atrium. The right atrium is in fluid communication with the superior vena cava and the inferior vena cava. The atrioventricular septum separates the right atrium from the right ventricle. The tricuspid valve contained within the atrioventricular septum provides communication between the right atrium and the right ventricle.

In the normal heart, contraction and relaxation of the heart muscle (myocardium) takes place in an organized fashion as electro-chemical signals pass sequentially through the myocardium from the sinoatrial (SA) node to the atrioventricular (AV) node and then along a well defined route which includes the His-Purkinje system into the left and right ventricles. The AV node lies near the ostium of the coronary sinus in the interatrial septum in the right atrium. The His-Purkinje system begins at the AV node and follows along the membranous interatrial septum toward the tricuspid valve through the atrioventricular septum and into the membranous interventricular septum. At about the middle of the interventricular septum, the His-Purkinje system splits into right and left branches which straddle the summit of the muscular part of the interventricular septum.

Sometimes abnormal rhythms occur in the heart which are referred to generally as arrhythmia. For example, a common arrhythmia is Wolff-Parkinson-White syndrome (W-P-W). The cause of W-P-W is generally believed to be the existence of an anomalous conduction pathway or pathways that connect the atrial muscle tissue directly to the ventricular muscle tissue, thus bypassing the normal His-Purkinje system. These pathways are usually located in the fibrous tissue that connects the atrium and the ventricle.

Other abnormal arrhythmias sometimes occur in the atria, which are referred to as atrial arrhythmia. Three of the most common atrial arrhythmia are ectopic atrial tachycardia, atrial fibrillation and atrial flutter. Atrial fibrillation can result in significant patient discomfort and even death because of a number of associated problems, including: an irregular heart rate which causes patient discomfort and anxiety, loss of synchronous atrioventricular contractions which compromises cardiac hemodynamics resulting in varying levels of congestive heart failure, and stasis of blood flow, which increases the likelihood of thromboembolism.

Efforts to alleviate these problems in the past have included significant usage of pharmacological treatments. While pharmacological treatments are sometimes effective, in some circumstances drug therapy has had only limited effectiveness and is frequently plagued with side effects, such as dizziness, nausea, vision problems and other difficulties.

An increasingly common medical procedure for the treatment of certain types of cardiac arrhythmia is catheter ablation. During conventional catheter ablation procedures an energy source is placed in contact with cardiac tissue to heat the tissue and create a permanent scar or lesion. During one procedure the lesions are designed to interrupt existing conduction pathways commonly associated with arrhythmias within the heart. The particular area for ablation depends on the type of underlying arrhythmia. One common ablation procedure treats atrioventricular nodal reentrant tachycardia (AVNRT). Ablation of fast or slow AV nodal pathways is disclosed in Singer, I., et al., "Catheter Ablation for Arrhythmias" *Clinical Manual of Electrophysiology*, pgs. 421–431 (1993). The use of electrode catheters for ablating specific locations within the heart has also been disclosed, for example in U.S. Pat. Nos. 4,641,649, 5,263,493, 5,231,995, 5,228,442 and 5,281,217.

Another medical procedure using ablation catheters with sheaths to ablate accessory pathways associated with W-P-W utilizing both a transseptal and retrograde approach is discussed in Saul, J. P., et al. "Catheter Ablation of Accessory Atrioventricular Pathways in Young Patients: Use of long vascular sheaths, the transseptal approach and a retrograde left posterior parallel approach" *Journal of the American College of Cardiology*, Vol. 21, no. 3, pgs. 571–583 (Mar. 1, 1993). Other catheter ablation procedures are disclosed in Swartz, J. F. "Radiofrequency Endocardial Catheter Ablation of Accessory Atrioventricular Pathway Atrial Insertion Sites" *Circulation*, Vol. 87, no. 2, pgs. 487–499 (February, 1993).

Ablation of a specific location within the heart requires the precise placement of the ablation catheter within the heart. Precise positioning of the ablation catheter is especially difficult because of the physiology of the heart, particularly because the heart continues to beat throughout the ablation procedures. Commonly, the choice of placement of the catheter is determined by a combination of electrophysiological guidance and fluoroscopy (placement of the catheter in relation to known features of the heart which are marked by radiopaque diagnostic catheters which are placed in or at known anatomical structures, such as the coronary sinus, high right atrium and the right ventricle).

Ablation procedures using guiding introducers to guide an ablation catheter to a particular location in the heart for treatment of atrial arrhythmia have been disclosed in U.S. Pat. Nos. 5,497,774, 5,427,119, 5,575,166, 5,640,955, 5,564,440 and 5,628,316. During these procedures, ablation lesions are produced in the heart as an element of the medical procedure.

The energy necessary to ablate cardiac tissue and create a permanent lesion can be provided from a number of different sources. Originally direct current was utilized although laser, microwave, ultrasound and forms of direct current (high energy, low energy and fulgutronization procedures) have also been utilized to perform ablation procedures. However, because of problems associated with the use of DC current, radiofrequency (RF) has become the preferred source of energy for ablation procedures. The use of RF energy for ablation has been disclosed, for example, in U.S. Pat. Nos. 4,945,912, 5,209,229, 5,281,218, 5,242,441, 5,246,438, 5,281,213 and 5,293,868. The use of RF energy with an ablation catheter contained within a transseptal sheath for the treatment of W-P-W in the left atrium is disclosed in Swartz, J. F. et al. "Radiofrequency Endocardial Catheter Ablation of Accessory Atrioventricular Pathway Atrial Insertion Sites" Circulation Vol. 87, pgs. 487–499 (1993). See also Tracey, C. N. "Radio Frequency Catheter Ablation of Ectopic Atrial Tachycardia Using Paced Activation Sequence Mapping" J. Am. Coll. Cardiol. Vol. 21, pgs. 910–917 (1993).

In addition to radiofrequency ablation catheters, thermal ablation catheters have been disclosed. During thermal ablation procedures a heating element, secured to the distal end of a catheter, heats thermally conductive fluid, which fluid then contacts the human tissue to raise its temperature for a sufficient period of time to ablate the tissue. A method and device for thermal ablation using heat transfer is disclosed in U.S. Pat. No. 5,433,708. Another thermal ablation procedure utilizing a thermal electrode secured to a catheter and located within a balloon with openings in that balloon to permit heated conductive fluid introduced into the balloon from the catheter to escape from the balloon for contact with the tissue to be ablated is disclosed in U.S. Pat. No. 5,505,730.

Conventional ablation procedures utilize a single distal electrode secured to the tip of an ablation catheter. Increasingly, however, cardiac ablation procedures utilize multiple electrodes affixed to the catheter body. These ablation catheters often contain a distal tip electrode and a plurality of ring electrodes as disclosed in U.S. Pat. Nos. 5,582,609, 5,487,385, 5,228,442, 4,892,102, 5,025,786, 5,327,905, and 5,354,297.

To form linear lesions within the heart using a conventional ablation tip electrode requires the utilization of procedures such as a "drag burn". During this procedure, while ablating energy is supplied to the tip electrode, the tip electrode is drawn across the tissue to be ablated, producing a line of ablation. Alternatively, a series of points of ablation are formed in a line created by moving the tip electrode incremental distances across the cardiac tissue. The effectiveness of these procedures depends on a number of variables including the position and contact pressure of the tip electrode of the ablation catheter against the cardiac tissue, the time that the tip electrode of the ablation catheter is placed against the tissue, the amount of coagulum that is generated as a result of heat generated during the ablation procedure and other variables associated with a beating heart, especially an erratically beating heart. Unless an uninterrupted track of cardiac tissue is ablated, unablated tissue or incompletely ablated tissue may remain electrically active, permitting the continuation of the reentry circuit which causes the arrhythmia.

It has been discovered that more efficient ablation may be achieved if a linear lesion of cardiac tissue is formed during a single ablation procedure. The production of linear lesions in the heart by use of an ablation catheter is disclosed in U.S. Pat. Nos. 5,487,385, 5,582,609 and Ser. No. 08/407,448. A specific series of linear lesions formed in the atria for the treatment of atrial arrhythmia are disclosed in U.S. Pat. No. 5,575,766.

The ablation catheters commonly used to perform these ablation procedures produce scar tissue at a selected location by physical contact of the cardiac tissue with an electrode of the ablation catheter. Conventional tip electrodes with adjacent ring electrodes cannot perform this type of procedure, however, because of the high amount of energy that is necessary to ablate sufficient tissue to produce a complete linear lesion. Also, conventional ring electrodes may leave holes or gaps in the linear ablation lesion when used to ablate cardiac tissue, which can provide a doorway through the lesion for the creation of a new reentry circuit.

An ablation catheter for use in the heart which contains a pair of intertwined helical electrodes is disclosed in U.S. Pat. No. 5,334,193. The helically wound electrode is affixed to the surface of the catheter body over a distance of about 8 cm. from the distal tip of the catheter body. Other helical electrodes are disclosed in U.S. Pat. Nos. 5,542,928, 4,776, 334, 5,047,026, 4,934,049, 4,860,769, and 4,161,952 and WO 95/10319.

During conventional ablation procedures, the ablating energy is delivered directly to the cardiac tissue by an electrode on the catheter placed against the surface of the tissue to raise the temperature of the tissue to be ablated. This rise in tissue temperature also causes a rise in the temperature of blood surrounding the electrode, which often results in the formation of coagulum on the electrode, which reduces the efficiency of the ablation electrode.

To achieve efficient and effective ablation, coagulation of blood that is common with conventional ablation catheters should be avoided. This coagulation problem can be especially significant when linear ablation lesions or tracks are produced because such linear ablation procedures conventionally take more time than ablation procedures ablating only a single location.

It is accordingly an aspect of the invention to disclose a catheter for ablating tissue within the human heart.

It is a still further aspect of the invention to disclose a catheter containing one or more electrodes located within a lumen in the catheter body useful for creating linear ablation lesions.

It is a still further aspect of the invention to disclose an ablation catheter containing one or more electrodes located within a lumen in the catheter and a plurality of openings in the surface of the catheter body in communication with the electrode.

It is a still further aspect of the invention to disclose an ablation catheter containing one or more electrodes located within a lumen in the catheter, a plurality of openings in the surface of the catheter in communication with the electrodes and a structure for the introduction of a conductive media through the lumen to contact the electrodes and then be expelled from openings in the catheter body.

It is a still further aspect of the invention to disclose an ablation catheter useful for formation of a linear ablation lesion within the heart utilizing a catheter body containing one or more electrodes located within a lumen in the catheter body, conductive media passing through the lumen conductively in contact with the electrodes, and openings in the catheter body through which the conductive media passes to contact cardiac tissue for ablation.

It is a still further aspect of the invention to disclose an ablation catheter containing a catheter body with one or more coiled electrodes located within a lumen, a plurality of openings in the surface of the catheter body in communication with the coiled electrodes and the lumen, a conductive media passing through the lumen substantially in contact with the coiled electrodes and a structure in the catheter body which controls the flow of the conductive media through the openings in the surface of the catheter body.

It is a still further aspect of the invention to disclose an ablation catheter for use in the formation of a linear ablation lesion within the heart utilizing a catheter body containing one or more electrodes located within a lumen in the catheter body, conductive media passing through the lumen substantially in contact with the electrodes, openings in the catheter body through which the conductive media passes to contact cardiac tissue for ablation and a structure for guiding the catheter to the location to be ablated.

It is a still further aspect of the invention to disclose an ablation catheter for use in the formation of a linear ablation lesion within the heart utilizing a catheter body containing one or more electrodes located within a lumen in the catheter body, conductive media passing through the lumen, wherein the conductive media is substantially in contact with the electrodes, openings in the catheter body through which the conductive media passes to contact the cardiac tissue to be ablated and a rail for guiding the ablation catheter to the location to be ablated.

It is a still further aspect of the invention to disclose an ablation catheter for use in the formation of a linear ablation lesion within the heart utilizing a catheter body containing one or more electrodes located within a lumen in the catheter body, conductive media passing through the lumen wherein the conductive media is substantially in contact with the electrodes, openings in the catheter body through which the conductive media passes to ablate the cardiac tissue and a guidewire for guiding the ablation catheter to the location to be ablated.

It is a still further aspect of the invention to disclose a method for ablation of cardiac tissue by use of an ablation catheter containing one or more electrodes within a lumen in a catheter body by passing conductive media through the lumen where the conductive media is substantially in contact with the electrode and expelling the conductive media through the openings in the catheter body to contact the cardiac tissue for ablation.

These and other aspects of the invention can be provided by the catheter for the mapping and ablation of cardiac tissue which is disclosed by the present invention.

SUMMARY OF INVENTION

The present invention relates to an ablation catheter for ablation of human tissue. The catheter includes a catheter body with proximal and distal ends containing one or more lumen extending through the catheter body from its proximal to, or near, its distal end. A plurality of openings is provided in the surface of the catheter in communication with one of the lumens. One or more electrodes are secured within the lumen inside the catheter body. A system for introduction of a conductive media into the lumen is provided such that the media is conductively in contact with the electrodes. The invention also includes a system to control the flow of the conductive media through the lumen and out through the openings in the surface of the catheter.

Preferably, the openings are extended in a linear line down the side of the catheter.

Preferably, the electrodes constitute one or more coiled electrodes extending down the length of the lumen inside the catheter body.

Preferably the energy source conducted by the conductive media is radiofrequency energy.

Also disclosed is a process for the ablation of human tissue, particularly for the production of a linear lesion in the heart. During the procedure an ablation catheter is introduced into the heart to a location to be ablated. The ablation catheter includes a catheter body, a lumen passing through the catheter body, a plurality of openings in the surface of the catheter in communication with the lumen, and one or more electrodes secured within the lumen of the catheter body. A conductive media is passed through the lumen of the catheter where it conductively contacts the electrode contained within the lumen. The flow of the conductive media through the lumen is controlled so that the media is expelled through the openings in the catheter body such that the conductive media contacts the tissue to be ablated. Energy, such as radiofrequency energy, is conducted from the electrode by the conductive media to the tissue to be ablated for a sufficient period of time to ablate the tissue.

Preferably the energy conducted by the conductive media forms a linear lesion in the tissue.

BRIEF DESCRIPTION OF THE DRAWINGS

FIG. 1 is a side view of the ablation catheter of the present invention.

FIG. 2 is a cross section, side view of a distal portion of the ablation catheter placed against tissue to be ablated.

FIG. 3 is an enlarged, side cross section view of the distal portion of the ablation catheter as shown in FIG. 2.

FIG. 4 is a cross section view of the ablation catheter taken along the line 4—4 in FIG. 3.

FIG. 5 is a cross section view of the ablation catheter taken along the line 5—5 in FIG. 3.

FIG. 6 is a side view of a distal portion of the ablation catheter showing a line of openings extending along a portion of the catheter body.

FIG. 7 is a side view of an alternative embodiment of the distal portion of the ablation catheter showing two lines of openings extending along a portion of the catheter body.

FIG. 8 is a cross section view of the distal portion of the ablation catheter showing an alternative embodiment of the present invention wherein the gap between individual coils of the electrode contained within the lumen varies from the proximal to the distal end of the electrode.

DETAILED DESCRIPTION OF THE PREFERRED EMBODIMENT

Figure 9:
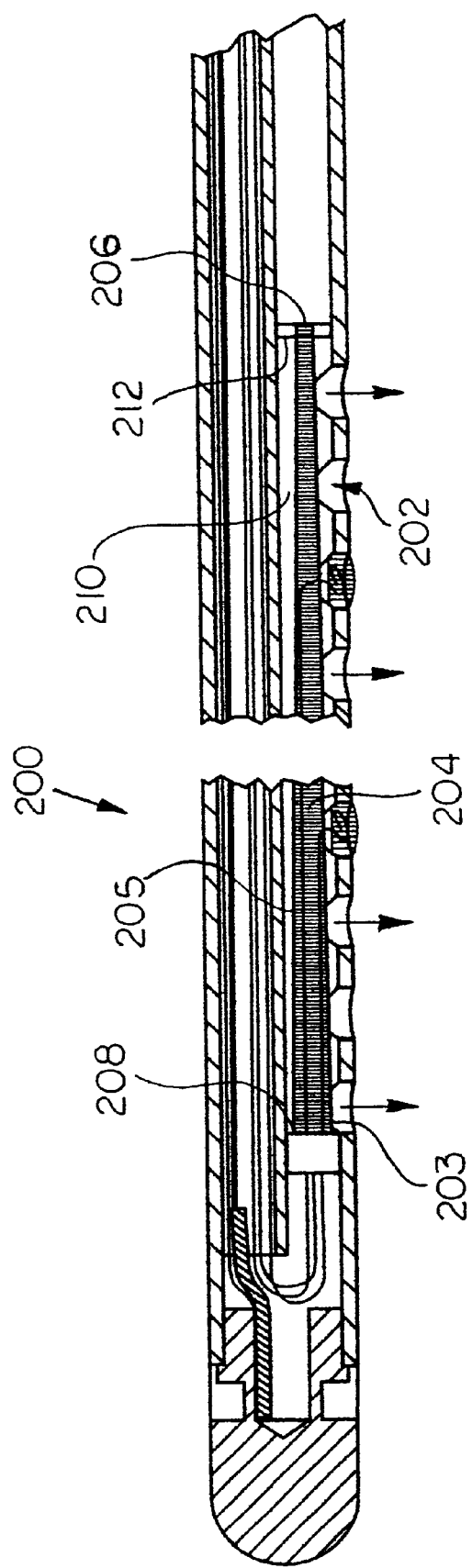
FIG. 9 is a cross section view of the distal portion of the ablation catheter in an alternative embodiment where the diameter of the electrode contained within the lumen increases from the proximal to the distal end of the electrode.

The ablation catheter (10) of the present invention as shown in FIGS. 1, 2 and 3 is comprised of a catheter body (12) with a proximal end (14) and a distal end (16), at least one lumen (18) extending lengthwise substantially through the catheter body (12), a plurality of openings (20) in the surface of the catheter body (12) extending through the outside surface (21) of the catheter body (12) into the lumen (18), an electrode (22), or plurality of electrodes, secured within the lumen (18), and a system for introduction of a conductive media into the lumen (18), whereby the conductive media contacts the electrode (22) or electrodes as the media passes through the lumen (18) and is expelled out the openings (20) in the catheter body (12) to contact tissue (23) to be ablated. There is also preferably provided a system to control the flow of the conductive media through the lumen (18) to create a reasonably consistent flow of conductive media out through substantially all of the openings (20) in the surface of the catheter body (12).

The catheter body (12) is a conventional elongated catheter made of materials suitable for use in humans, such as nonconductive polymers. Exemplary polymers used for the production of the catheter body include those well known in the art such as polyurethanes, polyether-block amides, polyolefins, nylons, polytetrafluoroethylene, polyvinylidene fluoride, and fluorinated ethylene propylene polymers and other conventional materials.

The length of the catheter (10) is preferably from about 50 cm to about 150 cm (20 to 60 in.). The diameter of the catheter (10) is within ranges well known in the industry, preferably, from about 4 to 16 French and more preferably from about 6 to 8 French (1 French equals ⅓ of a millimeter (0.013 in.)).

The catheter body (12) preferably contains one or more lumens extending through the catheter body (12) from its proximal end to near its distal end as shown in FIGS. 4 and 5.

Preferably, sufficient lumens are present in the catheter body (12) to accommodate wires for one or more sensing electrodes, preferably a single tip electrode (30), thermosensing devices, such as thermocouples (32), and the electrode (22) or electrodes used to contact the conductive media as shown in FIG. 3, as well as to accommodate the flow of the conductive media. In addition, in a preferred embodiment, one of the lumens also contains a system to control the movement of the ablation catheter. In one embodiment this system is a pull wire (24).

The lumen (18) of the catheter (10) in which the electrode (22) or electrodes are secured is in communication with the openings (20) and extends from the proximal end (14) of the catheter to near its distal end (16). The diameter of the lumen (18) should be sufficient to accommodate the electrode (22) or electrodes passing through the lumen, as well as to permit the flow of conductive media through the lumen (18) during the ablation procedure. Preferably, the lumen (18) should have a diameter of at least about 0.2 mm (0.008 in.) and preferably from about 0.3 mm (0.01 in.) to about 1.0 mm (0.04 in.).

There are preferably a plurality of openings (20) in the surface (21) of the distal portion (16) of the catheter (10), each of which are in communication with the lumen (18). Preferably, these openings (20) are formed into a linear line along the length of the catheter as shown in FIG. 6. The openings (20) can be of any size or shape that permit the passage of the conductive media through the lumen of the catheter without compromising the structural integrity of the catheter. The number of individual openings (20) of the catheter is from about 2 to about 100 individual openings, preferably 3 or more.

Preferably the openings (20) are circular in cross section with a diameter of about 0.25 mm (0.01 in) to about 2.5 mm (0.1 in). The distance between the openings (20) should be restricted such that sufficient conductive media is expelled through adjacent openings (20) to contact the tissue to be ablated and conduct sufficient radiofrequency energy to the tissue to form an adequate linear ablation lesion. In a preferred embodiment, the distance between the individual openings (20) does not exceed about 4.0 mm (0.16 in.) and preferably does not exceed from about 0.5 mm (0.02 in.) to about 1.5 mm (0.06 in.). The openings (20) extend substantially along the length of the catheter body (12) at least about 0.5 cm. (0.2 in.), preferably as much as about 6.0 cm. (2.4 in.).

In an alternative preferred embodiment, the openings (20) in the catheter body (12) are formed in a pair of linear lines approximately parallel to each other extending along the length of the catheter body (12) as shown in FIG. 7. By using a pair of linear lines, it is possible to form a wider ablation lesion. In a preferred embodiment, openings (20) are provided in the catheter body (12) through to the lumen (18) at or close to both the proximal end (27) and distal end (25) of that portion of the lumen which contains, or may contain, an electrode, as shown in FIG. 3. By this structure, the possibility of pooling of conductive media in the lumen is reduced. Such pooling could lead to hot spots within the lumen which may reduce the effectiveness of the ablation catheter. A portion of the electrode wire (34) which, may or may not be coated, connects to the electrode (22) and may be present within the lumen (18) at the point where the electrode wire is connected to the coils (26) of the electrode (22).

The electrode wire (34), which is secured to the electrode (22) or electrodes, passes through the catheter body (12) through a lumen (29) outside of the lumen (18) which contains the electrode (22) and enters the lumen (18) where it is secured to the electrode (22) or electrodes, preferably at the distal end of the electrode (22) by an adhesive seal (28) as shown in FIG. 3. The electrode (22) or electrodes extend through the lumen (18) at least about 4 mm. (0.15 in.) and preferably from about 1 cm. (0.4 in.) to about 6 cm. (2.4 in.). The electrode (22) can constitute a single electrode or multiple electrodes, preferably 2 to 5 electrodes, each of which are secured to separate electrode wires. For purposes of this discussion however, the electrode utilized is a single electrode, recognizing that multiple electrodes are an alternative embodiment.

In one preferred embodiment, the electrode (22) is in the form of a coiled electrode containing a series of individual coils (or turns) (26) as shown in FIG. 3. The coiled electrode (22) is formed from conventional electrode wire material, such as platinum or nickel, where the diameter of the wire which forms each of the coils (26) of the electrode (22) is preferably from about 0.02 mm (0.001 in) to about 0.4 mm (0.015 in). The individual coils (26) of the coiled electrode (22) are spaced sufficiently close to each other to contact the conductive media and thus conduct the energy, preferably radiofrequency energy, through the conductive media as it passes through the lumen (18) and over and around the coils (26) without unduly restricting the flow of the conductive media through the openings (20) in the catheter body (12). The flow around the coils should be sufficient to cool the electrode (22) or electrodes during the ablation procedure, which reduces the likelihood of formation of coagulum. Preferably, the flow of conductive media is maintained at a positive pressure throughout the ablation procedure to prevent any substantial flow of blood into the inside of the catheter body (12) where that blood might contact the electrode (22) or electrodes. The flow of conductive media is maintained by a conventional fluid flow pump (not shown) with a conventional stop cock and tubing (36).

By retaining the electrode (22) within the lumen (18) of the catheter (10) and by forcing the conductive media out the openings (20) in the catheter body (12) under a positive pressure, the electrode (22) does not directly contact the tissue or blood present in the chamber where the ablation procedure is performed. This reduces both coagulum buildup and the likelihood of clot formation. In addition, the electrode (22) is constantly being cooled by the passage of the conductive media through the lumen (18).

The electrode (22) contacts the conductive media as it passes through the lumen (18) of the catheter body (12). After such contact by the electrode, the conductive media passes through the openings (20) in the catheter body (12) to contact the cardiac tissue adjacent to the openings (20). The flow of the conductive media through these openings should be positive, preferably at least about 1 ml. per minute and more preferably about 10 ml. per minute. In a preferred embodiment, the conductive media is a conventional saline solution or other conductive media as are well known in the industry.

The preferred source for energy emitted by the electrode (22) is radiofrequency energy, although other sources for energy can be utilized including direct current, laser, ultrasound and microwave. During the ablation procedure the radiofrequency energy from the electrode is conducted by the conductive media to the tissue to be ablated. In one preferred embodiment, the impedance of the conductive media is less than that of the impedance of the human tissue so that the human tissue will heat to an ablation temperature at a faster rate than does the conductive media. If sufficient energy is conducted to the tissue for a sufficient period of time, a satisfactory ablation lesion is formed. The lesion being formed should have an adequate depth along the entire length of the lesion to avoid gaps that have been present with certain prior art ablation procedures.

The gap between individual coils of the coiled electrode may vary from no separation to a range of about 0.025 mm (0.001 in.) to about 0.5 mm. (0.02 in.). In addition, the gap (104) between the individual coils (106) may vary down the length of the electrode (108), as shown in FIG. 8.

The outside diameter of the electrode may also vary down the length of the electrode as shown in FIG. 9. The largest outside diameter (203) of the coiled electrode (204) is approximately equivalent to the diameter of the lumen (205) containing that electrode. The shape or angle of the coils along the length of the lumen is not particularly important and is generally a function of the pitch of the individual coils. Adjustments to the shape of the coils within the lumen which may affect the flow of the conductive media through the lumen are within the contemplation of this invention.

In order to form a consistent ablation lesion, it is important that the conductive media passing through the openings of the catheter body is expelled through substantially all of the openings. Any structural system which accomplishes this goal of controlling the flow of the conductive media through these openings is within the scope of this invention.

In one preferred embodiment of the ablation catheter (100) as shown in FIG. 8, control of the flow of the conductive fluid through the openings (102) in the ablation catheter (100) is accomplished by varying the gap (104) between individual, adjacent coils (106) of the electrode (108) along the length of the lumen (110). In this preferred embodiment, the gap (104) between individual adjacent coils (106) of the electrode (108) incrementally increases from virtually no space between the coils (106) at the proximal end (112) of the electrode (108), to a distance of about 0.0025 mm (0.0001 in.) to about 0.5 mm (0.02 in.) at the distal end (114) of the electrode (108).

When this structural system is utilized to control the flow of the conductive media, the conductive media is introduced into the proximal end (112) of the lumen (110) containing the electrode (108). Flow is inside the coils (106) of the electrode (106). More pressure is created on the flow of the conductive media by this structure at the proximal end (112) of the electrode (108) than at a location more distal because there is an increasing gap (104) between individual coils (106) along the length of the catheter (100) from proximal end (112) to distal end (114). This control of the flow of the conductive media through the inside of the coiled electrode (108) results in a reasonably consistent flow of the conductive media through and around the coils (106) of the electrode down the length of the catheter (100). By regulating the flow through the individual coils (106) of the electrode (108), a reasonably consistent flow of conductive media is also provided through the openings (102) in the surface of the catheter (100), as shown by arrows 115.

In a further alternative embodiment of the ablation catheter (200) or as an additional element of the previously discussed embodiment, the flow of the conductive fluid through the openings (202) of the catheter (200) can be controlled by varying incrementally the inner diameter of the inside space within the coils of the electrode (204) over its length, as shown in FIG. 9. When the inner diameter of the space inside the coiled electrode (204) increases, the resistance to flow of the conductive media through the electrode (204) decreases. In this embodiment, the inner diameter of the electrode (204) increases from about 0.05 mm (0.002 in) to about 2.5 mm (0.1 in) near the proximal end (206) of the electrode until it reaches its maximum outside diameter at its distal end (208), which is approximately equivalent to the diameter of the lumen (210), preferably about 0.2 mm (0.008 in) to about 2.5 mm (0.1 in).

To secure the electrode (204) within the lumen (210), the proximal end (206) of the electrode (200), or the most proximal end of the first electrode, if more than one electrode is used, is sealed in place within the lumen (210), preferably with an adhesive material (212). This adhesive material (212) also blocks the flow of the conductive media around the outside of the electrode (204) and forces the conductive media to flow inside the coils of the electrode (204) then flows out the gaps in the coil and out the openings (202) in the catheter (200), where the conductive media contacts the cardiac tissue to be ablated.

In another preferred embodiment which is a combination of the embodiments shown in FIGS. 8 and 9, the structure and shape of the electrode is modified by varying both the gap between the individual coils of the electrode over the length of the electrode and the inner diameter of individual coils of the electrode over the length of the electrode. By varying the structure of the electrode in this manner, the flow of the conductive media out of the openings can be controlled so that it is relatively consistent through substantially all of the openings in the catheter body.

Figure 10:
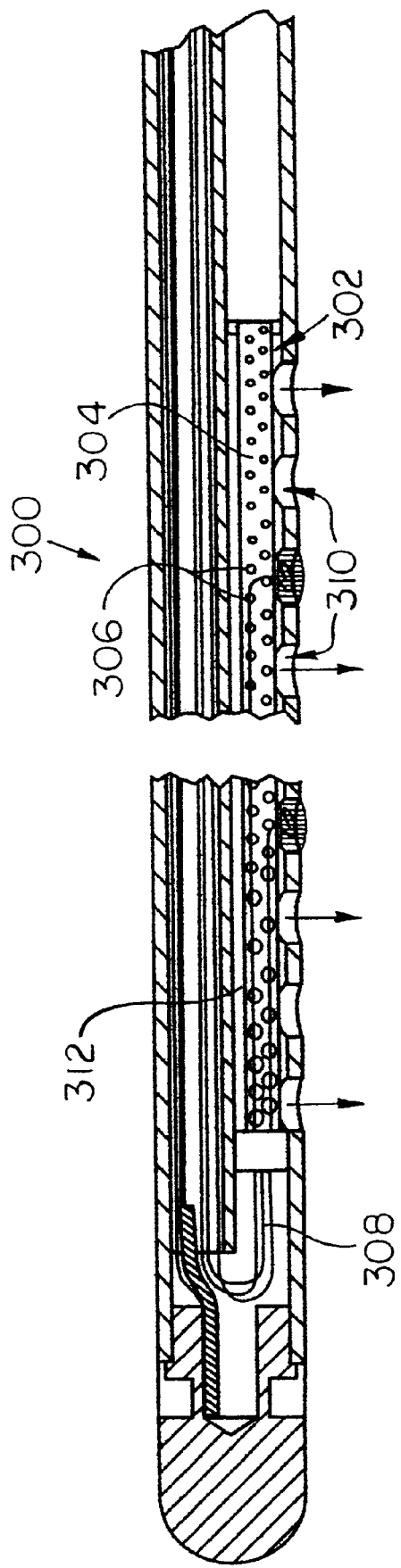
FIG. 10 is a cross section view of the distal portion of the ablation catheter in a further alternative embodiment where the electrode contained within the lumen includes a conductively coated tubular element containing a series of openings.

In a further preferred alternative embodiment of the ablation catheter (300) shown in FIG. 10, the electrode (302) of the catheter (300) includes a tubular body (304) coated with an electrically conductive coating and containing a series of openings (306) of varying sizes and/or spacing over the length of the tubular body (304). The tubular body (304) is produced from conventional flexible conductively coatable materials, such as polyurethanes, polyether-block amides, polyolefins, silicone, nylons, polytetrafluoroethylene, polyvinylidene fluoride, and fluorinated ethylene propylene polymers and other conventional materials. The conductive coating is applied by conventional methods, such as spraying, printing or vacuum deposition. In order to render the tubular body (304) electrically conductive, it is connected to a conventional electrode wire (308) by conventional procedures.

The size of the openings (306) in the tubular body (304) vary, preferably increasing incrementally over the length of the catheter (300). Preferably, the openings (306) vary from about 0.01 mm (0.0004 in) to about 1.0 mm (0.04 in). If the inside diameter of the tubular body (304) remains constant and the openings (306) in the tubular body (304) increase in size and/or spacing incrementally over the length of the tubular body (304), the rate of flow of the conductive media out of the openings (310) in the catheter body is generally consistent.

In one embodiment of the alternative embodiment, the tubular body (304) has an outside diameter approximately equal to the diameter of the lumen (312) of the catheter (300). Alternatively, the tubular body (304) may have an outside diameter slightly less than the diameter of the lumen (312) of the catheter which will permit the conductive fluid to pass through the openings (306) in the tubular body (304) to substantially around the tubular body and substantially fill the space within the lumen. The length of the tubular body (304) is preferably approximately the same length as that portion of the catheter (300) that contains openings (310) in the catheter body.

Figure 11:
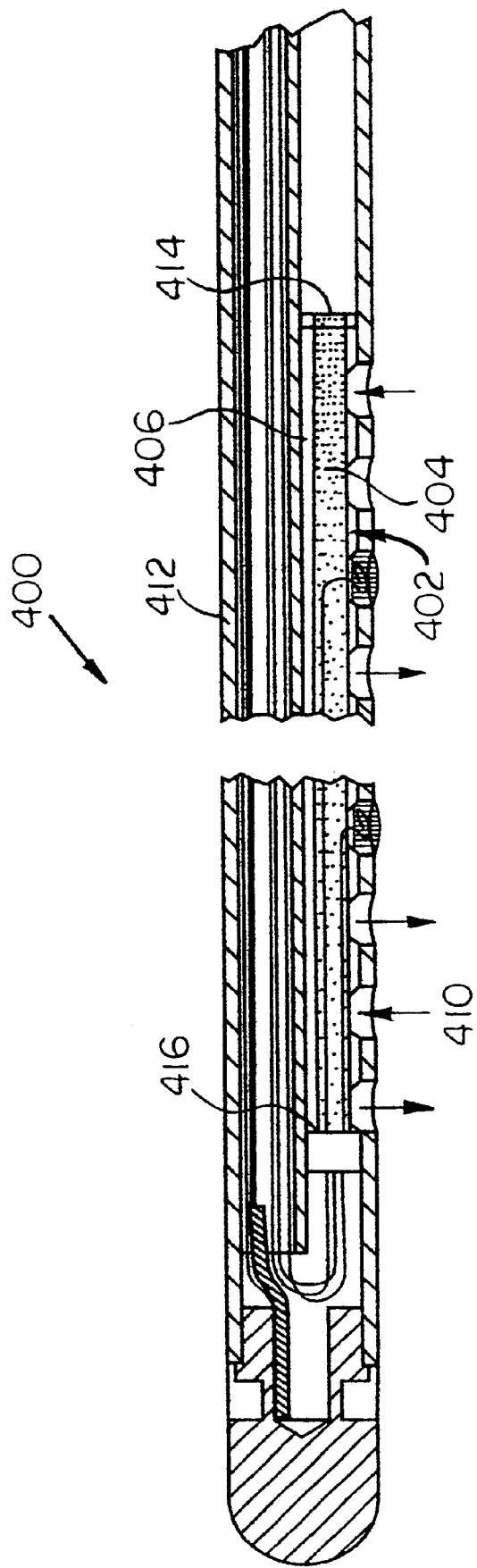
FIG. 11 is a cross section view of the distal portion of the ablation catheter showing a further alternative embodiment where the electrode contained within the lumen includes a filter element.

Referring to FIG. 11, a further alternative embodiment of the ablation catheter (400) is shown. The electrode (402) of the catheter (400) includes a tubular, porous conductive filter element (404) connected to a source of energy, preferably radiofrequency energy, such as a wire electrode (408). The conductive media passes through the tubular, porous conductive filter element (404) and is conductively contacted by the electrode. The conductive media then passes out the openings (410) in the catheter body (412). The diameter of the filter element (404) is approximately the same as the diameter of the lumen (406) of the catheter (400). The filter element (404) is constructed of material with a decreasing density from proximal end (414) to distal end (416) of the filter element (404) SO that the conductive media passes through the filter element (404) at a varying rate over the length of the filter element (404). The density of this filter element (404) over its length is adjusted by conventional means to equalize substantially the flow of the conductive media through the filter element (404).

Any system for contacting the conductive media with energy can be utilized with this conductive filter element. In one preferred embodiment a wire electrode (408) is passed through or around the conductive filter element (404). Alternatively, a conductive coating may be placed on or through the conductive filter element (404) which itself is attached to a wire electrode.

In a preferred embodiment, filter element (404) is produced from a material which controls the flow of the conductive media such as sintered metal, woven wire, felted stainless steel fiber or conductively coated engineered porous polymer materials, preferably a polypropylene microfiber.

Other embodiments of this invention which result in a method and device which controls the flow of the conductive media out the openings in the catheter body are also within the scope of this invention.

The ablation catheter may be guided to and held in the position necessary for the ablation procedure by conventional medical devices such as introducers. Alternatively, or in addition to the use of an introducer, and in a preferred embodiment, a system is utilized to assist the ablation catheter to move to the location for the ablation procedure. In one preferred embodiment as shown in FIG. 3, a pull wire (24) is secured into the catheter (10) through a lumen to be used to steer the ablation catheter (10). The structure and composition of the pull wire is conventional.

Alternatively, a guidewire (not shown) can be used to assist in the placement of the ablation catheter in the position necessary for the ablation procedure.

In another alternative embodiment, the structure of the ablation catheter can be modified to allow the ablation catheter to pass over a rail (not shown) which is introduced into the location for the ablation procedure.

Preferably, temperature sensors, such as thermistors or thermocouples (32) as shown in FIG. 3, are secured to the surface of the catheter to monitor the temperature of the tissue being ablated.

In addition to the electrode (22) used to contact the conductive media, a sensing electrode or electrodes to monitor electrical activity may be secured to the catheter, such as a tip electrode (30) secured at or near the distal tip of the catheter (10) as shown in FIG. 3. Preferably the tip electrode (30) is secured to an electrode wire passing through the catheter body (12) of the ablation catheter (10).

In operation, a modified Seldinger technique is normally used for the insertion of the associated dilators, introducers and ablation catheter into the body. The appropriate vessel is accessed by needle puncture. The soft flexible tip of an appropriately sized guidewire is then inserted through, and a short distance beyond, the needle into the vessel. Firmly holding the guidewire in place, the needle is removed. The guidewire is then advanced through the vessel into the appropriate portion of the heart for the ablation procedure. A preformed, shaped guiding introducer or guiding introducer system, such as those disclosed in U.S. Pat. No. 5,575,766, may be utilized to assist in proper placement of the ablation catheter (10) in the heart. Alternatively, or additionally, the ablation catheter (10) may contain a mechanism to make it steerable, such as a pull wire (24) as shown in FIG. 3, so that the ablation catheter (10) may be guided within the vessel or chamber of the human body to be ablated without use of a guiding introducer. The ablation catheter can also be directed to the location to be ablated by other steering mechanism, such as a rail or a guidewire.

In one embodiment, with a guidewire in place, the dilator is placed over the guidewire with the appropriate guiding introducer, or guiding introducer system. The dilator and the guiding introducer or guiding introducer system generally form an assembly to be advanced together along the guidewire into the appropriate vessel. After insertion of the assembly, the guidewire is then withdrawn.

The guiding introducer or guiding introducer system for use in the heart is then passed over the guidewire through its lumen and positioned to allow ablation and mapping procedures to be performed at the appropriate location in the heart. Once the guiding introducer or guiding introducer system is in place at the appropriate location within the heart, the ablation catheter (10) is advanced through the lumen of the guiding introducer or guiding introducer system.

After the desired location for ablation is determined, and the ablation catheter has been guided to that location, the portion of the catheter body (12) containing openings (20) is placed at or near the tissue (23) to be ablated as shown in FIG. 2. Placement of the portion of the catheter body containing the openings (20) against the tissue to be ablated is achieved by conventional procedures such as fluoroscopy, the use of markers or other conventional methods. A conductive media is then passed through the lumen (18) of the ablation catheter (10), where it passes around the electrode (22).

Several different embodiments exist for the structure of the electrode (22). In one preferred embodiment the electrode (22) is a coiled electrode, or a series of interconnected coiled electrodes, which may have the same or a different gap between the individual coils of the electrode, so that the flow of the conductive media through the openings (20) in the catheter body (12) is generally consistent over the length of the catheter body (12). Other alternative embodiments for the electrode (22) as discussed in the application can be utilized as long as the flow of the conductive media through the openings (20) over the length of the catheter body (12) is generally consistent.

After contact with the electrode, the conductive media then passes out through the openings (20) in the ablation catheter (10) where it contacts the tissue to be ablated. The conductive media conducts the energy, preferably radiofrequency energy, generated by the electrode (22) to the surface of the tissue to be ablated. The conductive media continues to pass through the openings (20) to contact the tissue for a sufficient period of time to permit the radiofrequency energy to form the ablation lesion or tract.

Thermosensing devices, such as thermocouples (32), are secured to the ablation catheter (10) to determine whether sufficient energy has been applied to the tissue to create an adequate linear lesion. After the ablation procedure is completed, a sensing electrode, such as a tip electrode (30), may be utilized as a sensing system to determine if the arrhythmia has been eliminated at the particular location within the heart. Additional ablation lesions or tracks can then be produced using the ablation catheter (10) at the same or different locations within the heart.

The device of the instant invention is designed to produce a linear lesion without exposing the surface of the ablation electrode to direct contact either with blood or cardiac tissue. In addition, the process disclosed herein provides an efficient procedure for the creation of linear lesions and ablation tracks without the associated problems present with prior art devices.

By retaining the electrode within the lumen of the catheter and by forcing the conductive media out the openings in the catheter body, the electrode does not directly contact the cardiac tissue or the blood present in the chamber where the ablation procedure is performed. This reduces both coagulum buildup and the likelihood of clot formation.

Pharmacological treatments may also be used in combination with ablation procedures to relieve the atrial arrhythmia.

It will be apparent from the foregoing that while particular forms of the invention have been illustrated and described, various modifications can be made without departing from the spirit and scope of the invention.

I claim:

1. An ablation catheter comprising
   (a) a catheter body with proximal and distal ends and an external surface,
   (b) a lumen within the catheter body,
   (c) a plurality of conductive media outlet openings in the external surface of the catheter body which are in communication with the lumen, wherein the conductive media outlet openings comprise a linear line of openings extended down the catheter body,
   (d) an electrode fixedly secured to the catheter body and located within the lumen,
   (e) an introduction system to introduce a conductive media into the lumen to contact the electrode, and
   (f) a conductive media flow control system structured to expel the conductive media through the conductive media outlet openings, wherein the conductive media flow control system is capable of regulating the flow of conductive media through the conductive media outlet openings to form a reasonably consistent flow of the conductive media through substantially all of the conductive media outlet openings.

2. The ablation catheter of claim 1 wherein the electrode comprises a plurality of individual electrodes.

3. The ablation catheter of claim 1 whereas the electrode comprises a coiled electrode.

4. The ablation catheter of claim 1 wherein the conductive media is a saline solution.

5. The ablation catheter of claim 1 further comprising a steering system to adjust the position of the catheter.

6. The ablation catheter of claim 5 wherein the steering system comprises a pull wire.

7. The ablation catheter of claim 1 wherein the introduction system comprises a fluid flow pump.

8. The ablation catheter of claim 1 further comprising a tip electrode.

9. An ablation catheter comprising
   (a) a catheter body with proximal and distal ends and an external surface,
   (b) a lumen within the catheter body,
   (c) a plurality of conductive media outlet openings in the external surface of the catheter body which are in communication with the lumen, wherein the conductive media outlet openings comprise a linear line of openings extended down the catheter body,
   (d) an electrode fixedly secured to the catheter body and located within the lumen,
   (e) an introduction system to introduce a conductive media into the lumen to contact the electrode, and
   (f) a conductive media flow control system structured to expel the conductive media through the conductive media outlet openings, wherein the conductive media flow control system is substantially contained within the lumen of the catheter body, and wherein the conductive media flow control system is capable of regulating the flow of conductive media through the conductive media outlet openings to form a reasonably consistent flow of the conductive media through substantially all of the conductive media outlet openings.

10. The ablation catheter of claim 9 wherein the electrode comprises a plurality of individual electrodes.

11. The ablation catheter of claim 9 whereas the electrode comprises a coiled electrode.

12. The ablation catheter of claim 9 wherein the conductive media is a saline solution.

13. The ablation catheter of claim 9 further comprising a steering system to adjust the position the catheter.

14. The ablation catheter of claim 13 wherein the steering system comprises a pull wire.

15. The ablation catheter of claim 9 wherein the introduction system comprises a fluid flow pump.

16. The ablation catheter of claim 9 further comprising a tip electrode.

17. A process for catheter ablation of human tissue comprising
   (a) introducing an ablation catheter into a location within the human body to be ablated, wherein the ablation catheter comprises a catheter body, a lumen within the catheter body, a plurality of conductive media outlet openings in an external surface of the catheter body which are in communication with the lumen, wherein the conductive media outlet openings comprise a linear line of openings extending down the catheter body, an electrode fixedly secured to the catheter body located within the lumen, an introduction system capable of introducing a conductive media into the lumen, and a conductive media flow control system structured to expel the conductive media through substantially all of the conductive media outlet openings, wherein the conductive media flow control system is capable of regulating the flow of conductive media through the conductive media outlet openings to form a reasonably consistent flow of the conductive media through substantially all of the conductive media outlet openings,
   (b) passing conductive media through the lumen of the catheter body to contact the electrode,
   (c) expelling the conductive media through substantially all of the conductive media outlet openings in the catheter body in a reasonably consistent flow to contact the human tissue, and
   (d) conducting energy from the electrode to the human tissue using the conductive media for a sufficient period of time to ablate the tissue.

18. The process of claim 17 further comprising forming a linear lesion in the human tissue.

19. A process for catheter ablation of human tissue comprising
   (a) introducing an ablation catheter into a location within the human body to be ablated, wherein the ablation catheter comprises a catheter body, a lumen within said catheter body, a plurality of conductive media outlet openings in an external surface of the catheter body which are in communication with the lumen, wherein the conductive media outlet openings comprise a linear line of openings extending down the catheter body and an electrode fixedly secured to the catheter body located within the lumen, an introduction system capable of introducing a conductive media into the lumen, and a conductive media flow control system structured to expel the conductive media through substantially all of the conductive media outlet openings, and wherein the conductive media flow control system is contained substantially within the lumen of the catheter body, and wherein the conductive media flow control system is capable of regulating the flow of conductive media through the conductive media outlet openings to form a reasonably consistent flow of the conductive media through substantially all of the conductive media outlet openings,
   (b) passing a conductive media through the lumen of the catheter body to contact the electrode,
   (c) expelling the conductive media through substantially all of the conductive media outlet openings in the catheter body in a reasonably consistent flow to contact the human tissue, and
   (d) conducting energy from the electrode to the human tissue using the conductive media for a sufficient period of time to ablate the tissue.

20. The process of claim 19 further comprising forming a linear lesion in the human tissue.

\* \* \* \* \*